United States Patent
Walter et al.

(10) Patent No.: US 7,842,286 B2
(45) Date of Patent: Nov. 30, 2010

(54) HAIR STYLING CREAM

(75) Inventors: Andrea Walter, Plochingen (DE); Manuela Hannich, Egelsbach (DE); Bianka Schmich, Buerstadt (DE); Marina Loifenfeld, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 891 days.

(21) Appl. No.: 11/607,197

(22) Filed: Dec. 1, 2006

(65) Prior Publication Data

US 2007/0202068 A1 Aug. 30, 2007

(30) Foreign Application Priority Data

Dec. 2, 2005 (EP) .................................. 05026340

(51) Int. Cl.
*A61Q 5/08* (2006.01)
(52) U.S. Cl. ................................ 424/70.15; 424/70.122
(58) Field of Classification Search ........................ None
See application file for complete search history.

(56) References Cited

U.S. PATENT DOCUMENTS

| | | | |
|---|---|---|---|
| 6,585,965 B1 * | 7/2003 | Carballada et al. | ......... 424/70.1 |
| 2002/0120989 A1 | 9/2002 | Gomes | |
| 2005/0036971 A1 | 2/2005 | Kohlhase et al. | |

FOREIGN PATENT DOCUMENTS

| | | |
|---|---|---|
| EP | 0818190 A2 | 1/1998 |
| EP | 1426027 A1 | 6/2004 |

OTHER PUBLICATIONS

International Search Report for PCT/IB2006/054535, Jul. 31, 2007 (6 pages).
Ullmann's Encyclopedia for Industrial Chemistry, 4th Edition, vol. 24, p. 3, "wax" or "wax-like."
International Cosmetic Ingredient Dictionary and Handbook, 10th Edition 2004, "Hair Fixatives."
International Cosmetic Ingredient Dictionary and Handbook, 10th Edition 2004, "Polyquaternium."

* cited by examiner

*Primary Examiner*—Jyothsna A Venkat
(74) *Attorney, Agent, or Firm*—Angela K. Haughey; Angela M. Stone

(57) ABSTRACT

The present invention relates to hair styling creams comprising a crosslinked silicone polymer; an alkoxylated compound selected from polyethylenoxides and polyalkoxylated silicone compounds; emulsifier; a fatty phase; and an aqueous phase. The cream can be transferred into rope-, thread-, or fiber-like structures when distributed in the hands. It gives a powdery feel after drying and improves stability and gloss of hair.

5 Claims, No Drawings

HAIR STYLING CREAM

FIELD OF THE INVENTION

The present invention relates to hair styling creams which can form rope-, thread-, or fiber-like structures when distributed in the hands and which contain crosslinked silicone polymers, alkoxylated compounds, emulsifiers, an aqueous phase, and a fatty phase.

BACKGROUND OF THE INVENTION

Hair styling products are used for creating individual hair styles and for temporarily holding them in place for a period of time. Hair styling cream products play an important role among styling products. They particularly find application in putting short to medium length hair in a fashionable hairstyle and impart hold and luster as well as stabilize, condition, and fix the hairstyle. They provide the hairstyle with shape and luster. Application of hair styling creams is usually based on the following principles. The creamy products can be squeezed out of a tube onto the hand or they can be taken out of a suitable container such as a jar with a screw lid with the fingers. The product is distributed on the surface of the hand and waxy ingredients are melted or at least considerably softened by the heat of the hand in combination with the shear energy of rubbing. The cream is worked into the hair in a softened or more or less liquid state. Solvents may evaporate on the hair and the remaining ingredients may harden to a solid or semi-solid consistency on the hair. The hairdo obtained has stability and hold and frequently improved shine and a wet-look appearance. Some unique styling products have the ability to form rope-, thread-, or fiber-like structures during the drying period when touched with a finger and pulling away the finger or when rubbed between two fingers or hands and pulling the fingers or hands apart. Such products allow for a very advantageous way of applying the product by placing a multitude of threads like a spider web on the hair which then can be worked very easily into the hair. It is a special challenge for the formulator to create a hair styling product with rope-, thread-, or fiber-forming effects which at the same time satisfies the basic properties expected from a hair styling aid such as giving hair stability, definition, hold and/or gloss. There is the risk of typical fiber-forming products that they may be too sticky or greasy during application or after drying on the hair. Hair creams often result in an unpleasant greasy or oily feeling of the hair. Therefore a need exists for rope-, thread-, or fiber-forming hair styling products with a more pleasant, less sticky, and less greasy or oily feeling to the touch during application and/or after working into the hair.

SUMMARY OF THE INVENTION

It has now been found that high performance hair styling cream products in emulsion form can be formulated by the use of a combination of crosslinked silicone polymer with selected alkoxylated compounds. The present invention is directed to hair styling creams comprising
(a) at least one crosslinked silicone polymer;
(b) at least one alkoxylated compound selected from polyethylenoxides and polyalkoxylated silicone compounds;
(c) at least one emulsifier;
(d) a fatty phase; and
(e) an aqueous phase.

The emulsions can be of any type, e.g., oil-in-water or water-in-oil. Preferred are oil-in-water emulsions. These and other features, aspects, and advantages of the present invention will become evident to those skilled in the art from a reading of the present disclosure.

DETAILED DESCRIPTION OF THE INVENTION

All percentages, parts, and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. All molecular weights as used herein are weight average molecular weights expressed as grams/mole, unless otherwise specified. Herein, "comprising" means that other ingredients and other steps which do not affect the end result can be added. This term encompasses the terms "consisting of" and "consisting essentially of." The compositions and methods of the present invention can comprise, consist of, and consist essentially of the essential elements and limitations of the invention described herein, as well as any of the additional or optional ingredients, components, steps, or limitations described herein.

The term "thread" is used herein synonymous for "rope" and "fiber."

The term "hydrophobic" as used herein, mean substances which are substantially water insoluble (e.g., less than 1% by weight at 25° C.), but soluble in the fatty phase, with the solubility in the fatty phase being higher than that in water or in the aqueous phase.

The term "hydrophilic" as used herein, means substances which are substantially water soluble and oil insoluble with the solubility in water or the aqueous phase being higher than that in the fatty phase.

The term "fatty phase" as used herein, means a phase comprising hydrophobic substances and which is separated from water or the aqueous phase.

The term "aqueous phase" as used herein, means a liquid phase which comprises water and can additionally comprise hydrophilic co-solvents and water soluble substances.

The term "room temperature" as used herein, means 25° C.

The term "wax" or "wax-like" as used herein, corresponds to the definition of "wax" in *Ullmanns Encyclopedia for Industrial Chemistry,* 4th Edition, Volume 24, page 3. According to this definition wax substances are plastic at 20° C., solid to brittle, gross to fine crystalline, transparent to opaque, but not glassy, melting over 40° C. without decomposition. They have a comparatively low viscosity above their melting point, have a consistency and solubility that is comparatively temperature dependent and are polishable with a gentle pressure.

Crosslinked Silicone Polymer

The preferred amount of crosslinked silicone polymers is at least 5% by weight, more preferred from about 5% to about 50% or from about 10% to about 25% by weight.

Crosslinked silicone polymers are polymers with a crosslinked silicone network. They are preferably elastomers. Elastomers are polymers with entropy elasticity (rubber-like elasticity). Elastomers typically can be repeatedly stretched at 20° C. at least up to the two-fold length and return almost to the original form after releasing the stretching force. Elastomers typically have a glass transition temperature (amorphous polymers) or a melting temperature (crystalline polymers) of below 0° C. Crosslinked silicone polymers are for example those with the INCI-names Dimethicone Crosspolymer, Acrylates/Bis-Hydroxypropyl Dimethicone Crosspolymer, Butyl Dimethiconemethacrylate/Methyl Methacrylate Crosspolymer, C30-45 Alkyl Cetearyl Dimethicone Crosspolymer, C30-45 Alkyl Dimethicone/Polycyclohexene Oxide Crosspolymer, Cetearyl Dimethicone/Vinyl Dimethicone Crosspolymer, Dimethicone Crosspolymer, Dimethicone Crosspolymer-2, Dimethicone Crosspolymer-3, Dimethicone/Divinyldimethicone/Silsesquioxane Crosspolymer, Dimethicone/PEG-10/15 Crosspolymer, Dimethicone/PEG-15 Crosspolymer, Dimethicone/PEG-10 Crosspolymer, Dimethicone/Phenyl Vinyl Dimethicone Crosspolymer, Dimethicone/Polyglycerin-3 Crosspolymer, Dimethicone/Titanate Crosspolymer, Dimethicone/Vinyl Dimethicone Crosspolymer, Dimethicone/Vinyltrimethylsiloxysilicate Crosspolymer, Dimethiconol/Methylsilanol/Silicate Crosspolymer, Diphenyl Dimethicone Crosspolymer, Diphenyl Dimethicone/Vinyl Diphenyl Dimethicone/Silsesquioxane Crosspolymer, Divinyldimethicone/Dimethicone Crosspolymer, Lauryl Dimethicone PEG-15 Crosspolymer, Lauryl Dimethicone/Polyglycerin-3 Crosspolymer, Methylsilanol/Silicate Crosspolymer, PEG-10 Dimethicone Crosspolymer, PEG-12 Dimethicone Crosspolymer, PEG-10 Dimethicone/Vinyl Dimethicone Crosspolymer, PEG-10/Lauryl Dimethicone Crosspolymer, PEG-15/Lauryl Dimethicone Crosspolymer, Silicone Quaternium-16/Glycidoxy Dimethicone Crosspolymer, Styrene/Acrylates/Dimethicone Acrylate Crosspolymer, Trifluoropropyl Dimethicone/PEG-10 Dimethicone Crosspolymer, Trifluoropropyl Dimethicone/Trifluoropropyl Divinyldimethicone Crosspolymer, Trifluoropropyl Dimethicone/Vinyl Trifluoropropyl Dimethicone/Silsesquioxane Crosspolymer, Trimethylsiloxysilicate/Dimethicone Crosspolymer, Trimethylsiloxysilicate/Dimethiconol Crosspolymer, Vinyl Dimethicone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer.

Most preferred crosslinked silicone polymers are compounds with the INCI-name Dimethicone Crosspolymer. These are polymers of Dimethicone crosslinked with C3 to C20 alkyl groups. Dimethicone is the INCI-name for fully methylated linear siloxane polymers end blocked with trimethylsiloxy units.

Alkoxylated Compounds

The preferred amount of alkoxylated compounds is at least about 0.5% by weight, more preferred from about 3% to about 50% by weight or from about 8% to about 20% by weight. A preferred weight ratio of crosslinked silicones (a) to the sum of alkoxylated compounds (b) is from about 1:1 to about 1:10 or from about 1:2 to about 1:6.

A first type of alkoxylated compounds are polyethylenoxides (also named polyethylenglycols or polyoxyethylene), e.g., with molecular weights from about 190 to about 20,000. Preferred polyethylenoxides are at least semi-solid or more preferred liquid at room temperature (25° C.) with molecular weights of for example from about 190 to about 1,000, more preferred from about 350 to about 700, or from about 500 to about 650 g/mol. Liquid polyethylenoxides are, for example, those of formula $H(OCH_2CH_2)_nOH$ with n=4 to 14, preferably n=8 to 12. Suitable polyethylenoxides are for example those with INCI-names PEG-4, PEG-6, PEG-7, PEG-8, PEG-9, PEG-10, PEG-12, and PEG-14, wherein PEG-10 and PEG-12 are preferred. Marketed products are, for example, Polyglykol 400 with a molecular weight of about 380 to about 420 or Polyglykol 600 with a molecular weight of about 570 to about 630 which are marketed by Clariant.

A second type of alkoxylated compounds are alkoxylated silicone compounds. These are silicone polymers comprising polyalkylene oxide groups which can be at the ends of a polysiloxane chain or pending from the polysiloxane chain. Preferred alkoxylated silicone compounds are silicone polymers with polypropylene oxide (polypropylene glycol) or more preferred with polyethylene oxide (polyethylene glycol) chains. The degree of alkoxylation is preferably from about 2 to about 40, or from about 5 to about 30, or from about 7 to about 20, or from about 10 to about 15. Preferred alkoxylated silicone compounds belong to one or more of the following classes: polydimethylsiloxanes with polyalkylenglycol side chains; bis-alkoxylated silicone compounds; polyalkoxylated silicone waxes; esters of fatty acids with polyalkoxylated silicone compounds and water insoluble polyalkoxylated silicone compounds.

Typical polydimethylsiloxanes with polyalkylenglycol side chains are those with INCI-names PEG-x Dimethicone. These are polyethylene glycol derivatives of polydimethylsiloxanes containing an average of x moles of ethylene oxide wherein x may be a number of, for example, from about 3 to about 20, e.g., 3, 7, 8, 9, 10, 12, 14, or 17.

Typical bis-alkoxylated silicone compounds are poly(dialkylsiloxanes) with two polyoxyalkylene groups. Preferred are ABA-type block-copolymers with a middle block B of polydimethylsiloxane end-blocked with polyethylene oxide and/or polypropylene oxide blocks A. The end-blocks can be unsubstituted, i.e., have hydroxy groups at the ends or they can be substituted, e.g., with ether, ester, or urethane groups or especially can be esterified with fatty acids. The degree of alkoxylation is preferably from about 2 to about 40, from about 10 to about 30 or more preferred from about 12 to about 20. Bis-alkoxylated silicone compounds are for example those of formula

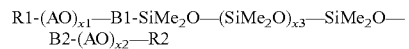

$$R1\text{-}(AO)_{x1}\text{—}B1\text{-}SiMe_2O\text{—}(SiMe_2O)_{x3}\text{—}SiMe_2O\text{—}B2\text{-}(AO)_{x2}\text{—}R2$$

wherein R1 is hydroxy, alkoxy with 1 to 22 C-atoms or carboxyalkyl with 2 to 22 C-atoms; B1 and B2 are different or preferably the same and are a single bond or divalent connecting group, especially an alkylene group with 1, 2, 3, or 4 C-atoms; AO is an oxyalkylene group, especially oxyethylene or oxypropylene; R2 is hydrogen or an alkyl group with 1 to 22 C-atoms which is esterified or etherified with the adjacent oxyalkylene group; x1 and x2 are numbers greater than or equal 1 and their sum represents the degree of alkoxylation and x3 is a number greater than or equal 1 representing the degree of polymerisation of the dimethylpolysiloxane. Bis-alkoxylated silicone compounds are for example those with INCI-names Bis-PEG-4 Dimethicone, Bis-PEG-12 Dimethicone, Bis-PEG-20 Dimethicone, Bis-PEG-12 Dimethicone Beeswax, Bis-PEG-12 Dimethicone Candellilate, Bis-PEG-15 Dimethicone/IPDI Copolymer, Bis-PEG-15 Methyl Ether Dimethicone, Bis-PEG-18 Methyl Ether Dimethylsilane, Bis-PEG/PPG-14/14 Dimethicone, Bis-PEG/PPG-20/20 Dimethicone, Bis-PEG/PPG-16/16 Dimethicone, Bis-PPG-7 Undeceneth-21 Dimethicone. Preferred are fatty acid esters of bis-(polyethylene oxide)-polydimethylsiloxane. Especially preferred are Bis-ethoxylated silicone waxes esterified with fatty acids, e.g., Bis-PEG-12 Dimethicone Beeswax.

Further alkoxylated silicone compounds include ethoxylated dimethylsilane methyl ether, e.g., water-dispersible silicone waxes of formula

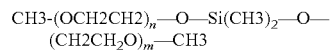

$$CH3\text{-}(OCH2CH2)_n\text{—}O\text{—}Si(CH3)_2\text{—}O\text{—}(CH2CH_2O)_m\text{—}CH3$$

wherein n and m can be the same or different, representing the degree of ethoxylation which is preferably from about 5 to about 40, especially from about 10 to about 20. An example is the compound with the INCI-name Bis-PEG-18 Methyl Ether Dimethyl Silane, which is marketed as Dow Corning® 2501 Cosmetic Wax.

Preferred types of alkoxylated silicones are those which are esterified with carboxylic acids, especially with fatty acids. Preferred fatty acids are monocarboxylic acids, dicarboxylic acids, and hydroxycarboxylic acids with at least 8 carbon atoms, preferably with about 10 to about 32 carbon atoms. Most preferred are the fatty acids derived from natural waxes, such as bees wax or candelilla wax. Esters of polyalkoxylated polydimethylsiloxanes are, for example, those with the INCI-names Bis-PEG-12 Dimethicone Beeswax, Bis-PEG-12 Dimethicone Candellilate, Dimethicone PEG-15 Acetate, Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phtalate, Dimethicone PEG-8 Phtalate, Dimethicone PEG/PPG-20/23 Benzoate, Dimethicone PEG-8 Succinate, Dimethicone PEG-7 Undecylenate. Most preferred are the fatty acid esters of bis-(polyethylene oxide)-polydimethylsiloxanes.

In one embodiment of the invention the hair styling cream comprises at least two alkoxylated compounds wherein at least one first alkoxylated compound is selected from polyethylenoxides, preferably with a molecular weight in the range of from 500 to 700 and at least one second alkoxylated compound is selected from alkoxylated silicones, preferably fatty acid esters of bis-(polyethylene oxide)-polydimethylsiloxane. A preferred weight ratio of polyethylenoxide to alkoxylated silicones is from about 0.5:1 to about 4:1 or from about 1:1 to about 3:1.

Emulsifier

The emulsifiers are preferably contained in an amount of from about 0.5% to about 20% by weight, especially from about 0.5% to about 15% by weight or from about 0.5% to about 5% by weight. Preferred emulsifiers are selected from the group of non-ionic and anionic surfactants. In a particularly preferred embodiment at least one or all of the emulsifiers have a wax-like consistency and a liquifying point above 25° C.

Nonionic emulsifiers are, for example:

alkoxylated fatty alcohols such as C8- to C30- or preferably C8- to C22-alcohols, alkoxylated fatty acids or alkoxylated fatty acid glycerides such as C12 to C22-fatty acids, alkoxylated alkylphenols (e.g., alkyl groups with 8 to 15 carbon atoms); typical degrees of ethoxylation being from 2 to 100 or 4 to 30 and typical degrees of propoxylation being from 1 to 5;

C8 to C30-, preferably C12- to C22-fatty acid glycerolmono- or diester, ethoxylated with from 1 to 30 mole ethylenoxide;

Castor oil or hydrogenated castor oil ethoxylated with from 5 to 60 mole ethylenoxide;

fatty acid sugar mono- or diester, especially ester of sucrose with one or two C8- to C30 or C12 to C22-fatty acid, INCI: Sucrose Cocoate, Sucrose Dilaurate, Sucrose Distearate, Sucrose Laurate, Sucrose Myristate, Sucrose Oleate, Sucrose Palmitate, Sucrose Ricinoleate, Sucrose Stearate;

ethoxylated sorbitan esters such as ester of sorbitan with one, two, or three C8- to C22-fatty acid and a degree of ethoxylation of from 4 to 20;

polyglyceryl fatty acid ester, especially of one, two, or more C8- to C22-fatty acids with polyglycerol of preferably 2 to 20 glycerol units;

alkylglucoside, alkyloligoglucoside or alkylpolyglucoside with C8- to C22-alkyl groups, e.g., Decyl Glucoside or Lauryl Glucoside.

Anionic surfactants are for example alkyl carboxylic acids, alkyl ethersulfates, alkylsulfates, sulfosuccinates, fatty acid isethienates, phosphoric acid alkyl ester, ethoxylated phosphoric acid alkyl ester such as mono- or diesters of phosphoric acid with C8- to C22-fatty alcohols ethoxylated with 2 to 30 mol ethylenoxide, acylaminoacids, said acyl groups having preferably 8 to 30 carbon atoms.

Preferred emulsifiers are nonionic and selected from ethoxylated fatty alcohols, ethoxylated nonylphenol, alkylpolyglycosides, fatty acid mono- or di-glycerides, ethoxylated hydrogenated or non-hydrogenated castor oil, fatty acid alkanolamides, polyethylene glycol esters of fatty acids. Preferred emulsifiers are also triesters of phosphoric acid with ethoxylated fatty alcohols such as, for example, the triester of phosphoric acid with cetyl and stearyl alcohol ethoxylated with 4 mol of ethylenoxide (INCI: Triceteareth-4 Phosphate).

Fatty Phase: Fats, Oils, Waxes

The fatty phase comprises at least one hydrophobic compound. The total amount of hydrophobic compounds is preferably at least about 5% by weight and up to about 60% by weight, for example, from about 10% to about 60% or from about 15% to about 50% by weight based on the total composition. Typical hydrophobic compounds include hydrophobic waxes, hydrophobic soft waxy or semi-solid materials and hydrophobic oils. Suitable hydrophobic waxes are, e.g., animal, vegetable, mineral and synthetic waxes, microcrystalline waxes, macrocrystalline waxes, solid paraffins, ozocerite, ceresine, montan wax, fischer-tropsch waxes, polyolefin waxes, e.g., polybutene, bees wax, wool wax (lanolin) and its derivative compounds, such as wool wax alcohol, candelilla wax, carnauba wax, Japan wax, hardened fats, fatty acid esters, fatty acid glycerides, polyethylene waxes and silicone waxes each with a solidification point of preferably above about 40° C., more preferably above 55° C. Suitable hydrophobic soft waxy or semi-solid materials are for example semi-solid paraffins. The solidification point of these paraffins is usually in a range of from about 25° C. to about 40° C. Products with an INCI name Petrolatum, e.g., VASELINE®, are especially suitable as the hydrophobic additive substance. This latter product is a semi-solid mixture of hydrocarbons obtained from petroleum.

Hydrophobic oils are liquid at room temperature. They can be volatile or low- or non-volatile. Suitable low-volatile or non-volatile hydrophobic oils have a melting point of under 25° C. and a boiling point preferably above 250° C., especially preferably above 300° C. Typical volatile oils have a melting point of under 25° C. and a boiling point preferably between about 25° C. and about 250° C. Oils generally known to one skilled in the art can be used, for example vegetable oils, animal oils, mineral oils (paraffinum liquidum), silicone oils, hydrocarbon oils, hydrogenated polyolefins, fatty alcohols with at least 8 carbon atoms including branched alcohols such as guerbet alcohols, oils from fatty acids and polyols (especially triglycerides), oils from fatty acids and monohydric C1- to C30-alcohols (preferred C3- to C22-alcohols) and mixtures of said hydrophobic oils. Non-limiting hydrophobic oils are for example cyclic paraffins, paraffin oils, isoparaffin oils, polydecene, mineral oil, isohexadecane, dodecane, isoeicosane, isocetylpalmitate, isopropylmyristate, isopropylpalmitate, isopropylstearate, octylisostearate, octylcocoate, octylpalmitate, octyldodecylmyristate, caprylic/capric triglyceride, butyloctanol, hexyloctanol, butyldecanol, hexyldecanol, octyldodecanol, hexyldecanol, stearylheptanoate, isohexyldecanoate, isodecyloctanoate, dibutyladipate, dicaprylylether, C12-15-alkylbenzoate, hydrogenated polyisobutene, squalane, squalene, native oils such as jojoba oil, olive oil, sunflower oil, soybean oil, peanut oil, rape seed oil, sweet almond oil, palm-oil, coconut oil, castor oil, hydrogenated castor oil, wheat germ oil, grape seed oil, safflower oil, evening primrose oil, macedemia nut oil, corn oil, avocado oil, lanolin oils, and similar oils. Especially preferred oil compounds are hydrocarbon oil such as mineral oil (e.g., paraffinum liquidum) and branched C8 to C30 alkyl alcohols. Silicone oils include polydimethylsiloxanes, phenylated silicones, polyphenylmethylsiloxanes, phenyltrimethicones, poly-C1 to C20-alkylsiloxanes, and alkylmethylsiloxanes. Suitable liquid silicone oils are linear or cyclic polydimethylsiloxanes, phenylated silicones, polyphenylmethylsiloxanes, phenyltrimethicones, poly(C1-C20)-alkylsiloxanes, alkylmethylsiloxanes. Specific examples of volatile oils are volatile hydrocarbons with boiling points up to 250° C. or cyclic siloxanes such as cyclooctamethyl tetrasiloxane or cyclodecamethyl pentasiloxane or linear siloxanes, such as hexamethyl disiloxane.

Preferred components of the fatty phase are selected from hydrocarbon compounds, fatty alcohols, fatty acid triglycerides and silicone oils.

Aqueous Phase

The aqueous phase primarily contains water. The amount of water is preferably from about 10% to about 70%, or from about 15% to about 60% or from about 20% to about 50% by weight. The aqueous phase can additionally contain hydrophilic organic solvents, such as monohydric or polyhydric C1 to C5-alcohols, especially ethanol, propanol, glycerol or glycols such as ethylene glycol or propylene glycol, in an amount of for example up to about 10% by weight, preferably from about 0.1% to about 8% by weight. The pH can be for example from about 6 to about 8 or from about 6.5 to about 7.5.

Hair Fixing Polymers

In one embodiment of the invention, the hair styling cream additionally comprises at least one hair fixing polymer. The amount of hair fixing polymer is preferably at least about 0.1% by weight, e.g., from about 0.1% to about 25%, or from about 0.5% to about 20%, or from about 1% to about 18% by weight based on the total composition. The hair fixing polymer can be nonionic, anionic, cationic, amphoteric, or zwitterionic, preferably it is nonionic. The hair fixing polymer can be synthetic or natural. The term "natural polymer" also comprises chemically modified polymers of natural origin. Preferred are polymers which are soluble in the aqueous phase. Hair fixing polymers are polymeric compounds which impart hair-holding or style-retention properties to hair, e.g., when applied as 0.01% to 5% by weight aqueous, alcoholic or aqueous-alcoholic solution or dispersion. In particular, hair fixing polymers are those polymers listed in the International Cosmetic Ingredient Dictionary and Handbook, 10$^{th}$ edition 2004 with the function "Hair Fixatives."

Suitable synthetic, non-ionic hair fixing polymers are for example:

homo- or copolymers of at least one monomer selected from vinyl pyrrolidone; vinyl caprolactam; vinyl ester (e.g., vinyl acetate), vinyl alcohol, acrylamide, methacrylamide, alkyl- and dialkyl acrylamide, alkyl- and dialkyl methacrylamide, dialkylaminoalkyl methacrylamide, dialkylaminoalkyl acrylamide, alkylacrylate, alkylmethacrylate, propylene glycol or ethylene glycol, wherein preferred alkyl groups of these monomers are C1- to C7-alkyl groups, more preferred C1- to C3-alkyl groups. Suitable are, e.g., homopolymers of vinyl caprolactam, homopolymers of vinyl pyrrolidone, homopolymers of N-vinyl formamide. Suitable hair fixing polymers are also copolymers of vinyl pyrrolidone and vinyl acetate; terpolymers of vinyl pyrrolidone, vinyl acetate and vinyl propionate; terpolymers of vinyl pyrrolidone, vinyl caprolactam and dialkylaminoalkyl(meth)acrylate; terpolymers of vinyl pyrrolidone, vinyl caprolactam and dialkylaminoalkyl(meth)acrylamide; polyacrylamide; polyvinyl alcohol; and hair fixing polyethylen glycol/polypropylen glycol copolymers. Preferred are nonionic vinyl lactam homo- or copolymers. Suitable vinyl lactams are, e.g., vinyl caprolactam and vinylpyrrolidone. Especially preferred are polyvinyl pyrrolidone, polyvinyl caprolactam, and polyvinyl pyrrolidone/vinyl acetate copolymers which are marketed, e.g., as Luviskol® VA 37 and Luviskol® VA 64.

Suitable synthetic, anionic hair fixing polymers can be synthetic or natural homo- or copolymers from monomeric units with acid groups. The monomers with acid groups can be copolymerized with monomers without acid groups. Preferred acid groups are —COOH, —SO$_3$H, —OSO$_3$H, —OPO$_2$H and —OPO$_3$H$_2$, carboxylic acid being most preferred. The acid groups can be unneutralized, partially neutralized or completely neutralized. Preferred is a degree of neutralization of from about 50% to about 100%. Suitable monomers are ethylenically unsaturated, radically polymerisable compounds carrying at least one acid group, e.g., styrene sulfonic acid, 2-acrylamide-2-methylpropane sulfonic acid, or carboxyvinyl monomers like acrylic acid, methacrylic acid, crotonic acid, fumaric acid, maleic acid, maleic anhydride and its monoesters or itaconic acid.

Comonomers without acid groups are, e.g., acrylamide, methacrylamide, alkyl- and dialkyl acrylamide, alkyl- and dialkyl methacrylamide, alkylacrylate, alkylmethacrylate, vinyl caprolactone, vinyl pyrrolidone, vinyl ester, vinyl alcohol, propylene glycol or ethylene glycol, amine substituted vinyl monomers such as dialkylaminoalkyl acrylate, dialkylaminoalkyl methacrylate, monoalkylaminoalkyl acrylate and monoalkylaminoalkyl methacrylate, wherein preferred alkyl groups are C1- to C7-alkyl groups, especially C1- to C3-alkyl groups.

Suitable anionic hair fixing polymers are in particular copolymers of acrylic or methacrylic acid with monomers selected from acrylic acid esters, methacrylic acid esters, acrylamides, methacrylamides and vinyl pyrrolidone; homopolymers of crotonic acid; copolymers of crotonic acid with monomers selected from vinyl esters, acrylic acid esters, methacrylic acid esters, acrylamides, methacrylamides. A natural anionic hair fixing polymer is shellac. Preferred anionic hair fixing polymers are vinylacetate/crotonic acid copolymer; partially esterified copolymers of vinyl methylether and maleic anhydride; terpolymers of acrylic acid, alkyl acrylate and N-alkyl acrylamide, e.g., acrylic acid/ethyl acrylate/N-t-butyl acrylamide terpolymer; terpolymers of vinyl acetate, crotonic acid and vinyl alkanoate, e.g., vinyl acetate/crotonic acid/vinyl neodecanoate copolymer.

Suitable synthetic, amphoteric hair fixing polymers are polymers with anionic or acidic functional groups as well as cationic or basic functional groups. The acidic or anionic functional groups are those as defined above for the anionic polymers. Cationic or basic functional groups are in particular primary, secondary, or tertiary amine groups or quaternary ammonium groups. Preferred examples are copolymers of alkyl acrylamide (especially octyl acrylamide), alkylaminoalkyl methacrylate (especially t-butylaminoethyl methacrylate) and two or more monomers selected from acrylic acid, methacrylic acid and their esters, wherein the alkyl-groups have from 1 to 4 C-atoms and at least one of the monomers has an acid group. A marketed product is, e.g., Amphomer® or Amphomer® LV-71 of National Starch. Further examples for hair fixing polymers are copolymers of acrylic acid, methyl acrylate and methacrylamidopropyl trimethylammonium chloride (INCI-name: polyquaternium-47); copolymer of acrylamidopropyl trimethylammonium chloride and acrylates; or copolymers of acrylamide, acrylamidopropyl trimethylammonium chloride, 2-amidopropyl acrylamide sulfonate and dimethylaminopropyl amine (INCI-name: polyquaternium-43). Suitable are also polymers with betaine groups, e.g., copolymers of methacryloyl ethylbetaine and two or more monomers selected from acrylic acid and its alkyl esters (INCI-name Methacryloyl Ethyl Betaine/Acrylates Copolymer).

Suitable cationic hair fixing polymers are polymers with cationic or basic functional groups. Cationic or basic functional groups are in particular primary, secondary, or tertiary amine groups or quaternary ammonium groups. The cationic charge density is preferably from 1 to 7 meq/g. The cationic polymers can be homopolymers or copolymers wherein the cationic or basic functional group can be part of the polymeric backbone or can be a pendant group. Monomers with cationic or basic groups can be copolymerised with monomers without cationic or basic group.

Suitable cationic monomers are ethylenically unsaturated radically polymerisable compounds with at least one cationic or basic group, e.g., ammonium substituted vinyl monomers such as trialkyl methacryloxy alkylammonium, trialkyl acryloxy alkyl ammonium, dialkyl diallyl ammonium and quaternary vinyl ammonium monomers with cyclic nitrogen containing groups such as pyridinium, imidazolium or quaternary pyrrolidones, e.g., alkylvinyl imidazolium, alkylvinyl pyridinium. The alkyl groups of these monomers are preferably lower alkyl groups such as C1 to C7 alkyl groups, more preferred C1 to C3 alkyl groups. The cationic monomers can be polymerised with non-cationic comonomers. Non-cationic comonomers are, e.g., acrylamide, methacrylamide, alkyl- and dialkyl acrylamide, alkyl- and dialkyl methacrylamide, alkylacrylate, alkylmethacrylate, vinyl caprolactone, vinyl pyrrolidone, vinyl ester such as vinyl acetate, vinyl alcohol, propylen glycol or ethylen glycol, wherein preferred alkyl groups are C1- to C7-alkyl groups, especially C1- to C3-alkyl groups.

Suitable cationic hair fixing polymers are for examples those listed in the *International Cosmetic Ingredient Dictionary and Handbook,* 10$^{th}$ edition 2004 as polyquaternium, e.g., methylvinyl imidazolium chloride/vinyl pyrrolidone copolymer (Polyquaternium-16) or quaternised vinyl pyrrolidone/dimethylaminoethyl methacrylate copolymer (Polyquaternium-11). Preferred synthetic cationic hair fixing polymers are: poly(dimethyl diallyl ammonium chloride); copolymers of acrylamide and dimethyl diallyl ammonium chloride; quaternary ammonium polymers made by reaction of diethylsulfate and a copolymer of vinyl pyrrolidone and dimethylaminoethyl methacrylate (e.g., GAFQUAT® 755 N, GAFQUAT® 734); quaternary ammonium polymers of methylvinyl imidazolium chloride and vinyl pyrrolidone (e.g., LUVIQUAT® HM 550); Polyquaternium-35; Polyquaternium-57; polymer of trimethylammoniumethyl methacrylate chloride; terpolymer of dimethyl diallyl ammonium chloride, sodium acrylate and acrylamide (e.g., MERQUAT5 Plus 3300); copolymer of vinyl pyrrolidone, dimethylaminopropyl methacrylamide and methacryloyl aminopropyllauryl dimethyl ammonium chloride; terpolymer of vinylpyrrolidone, dimethylaminoethyl methacrylate and vinyl caprolactam (e.g., GAFFIX® VC 713); vinyl pyrrolidone/methacryl amidopropyl trimethylammonium chloride copolymer (e.g., GAFQUAT® HS 100); copolymer of vinyl pyrrolidone and dimethylaminoethyl methacrylate; copolymer of vinyl pyrrolidone, vinyl caprolactam and dimethylaminopropyl acrylamide; poly- or oligoester made of at least one monomer selected from hydroxyacids which are substituted with at least one quaternary ammonium group.

Suitable cationic polymers derived from natural polymers are for example cationic derivatives of polysaccharides such as cationic derivatives of cellulose, starch or guar. Suitable are also chitosan and chitosan derivatives. Cationic polysaccharides have for example the general formula

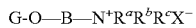

$$G\text{-}O\text{---}B\text{---}N^+R^aR^bR^cX^-$$

wherein G is an anhydroglucose group such as starch anhydroglucose or cellulose anhydroglucose; B is a divalent bridging group such as alkylen, oxyalkylen, polyoxyalkylen or hydroxyalkylen; $R^a$, $R^b$ and $R^c$ are independent from one another alkyl, aryl, alkylaryl, arylalkyl, alkoxyalkyl or alkoxyaryl with each up to 18 carbon atoms, wherein the total number of carbon atoms in $R^a$, $R^b$ and $R^c$ is preferably a maximum of 20; X is a counter ion, such as halogen, acetate, phosphate, nitrate or alkylsulfate, preferably chloride. Cationic cellulose polymers are, for example, those with the INCI-names Polyquaternium-10 or Polyquaternium-24. A cationic guar derivative is for example that with the INCI-name Guar Hydroxypropyltrimonium Chloride.

Especially preferred cationic hair fixing polymers are chitosan, chitosan salts, and chitosan derivatives. Chitosans are totally or partially deacetylated chitines. The molecular weight can be for example from about 20,000 to about 5 Millionen g/mol, e.g., from 30,000 to 70,000 g/mol for lower molecular weight chitosan. Preferred are high molecular chitosans with a molecular weight above 100,000 g/mol, more preferred from 200,000 to 700,000 g/mol. The degree of deacetylation is preferably from 10% to 99%, more preferred from 60% to 99%. A preferred chitosan salt is chitosonium pyrrolidonecarboxylate, e.g., KYTAMER® PC with a molecular weight of about 200,000 to 300,000 g/mol and a degree of deacetylation of 70% to 85%. Chitosan derivatives are, for example, quaternised chitosans, alkylated chitsoans, or hydroxyalkylated chitsoans such as hydroxyethyl-, hydroxypropyl- or hydroxybutyl chitosan. The chitosan or chitosan derivatives are preferably partially or completely neutralized. The degree of neutralization is preferably at least 50%, more preferred from 70% to 100%, based on the total number of amino groups. In principle, all cosmetic acceptable inorganic or organic acids can be used for neutralization, such as formic acid, tartaric acid, malic acid, lactic acid, citric acid, pyrrolidone carboxylic acid, glycolic acid, hydrochloric acid, etc., pyrrolidone carboxylic acid being especially preferred.

Preferred cationic polymers on a natural basis are:

cationic cellulose derivatives made from hydroxyethylcellulose and diallyl dimethyl ammonium chloride; cationic cellulose derivatives made from hydroxyethylcellulose and trimethyl ammonium substituted epoxide; chitosan and its salts; hydroxyalkyl chitosan and its salts; alkylhydroxyalkyl chitosan and its salts; N-hydroxyalkyl chitosan alkylether.

Most preferred hair fixing polymers are nonionic and selected from vinyllactam homo- or copolymers. These polymers are made from at least one vinyllactam monomer such vinylpyrrolidone or vinylcaprolactam. Examples are polyvinylpyrrolidone (INCI-name PVP; trade names, e.g., Luviskol® K30, K85, K90 available from BASF); copolymers of vinylpyrrolidone and vinylacetate (INCI-name VP/VA copolymer; trade names, e.g., Luviskol® VA37, VA64 available from BASF); copolymers of vinylpyrrolidone, methacrylamide, and vinylimidazole (INCI-name VP/Methacrylamide/Vinyl Imidazole Copolymer, trade name Luviset® Clear available from BASF).

Viscosity Modifying Agent

In one embodiment of the invention, the hair styling cream comprises at least one additional viscosity modifying agent which can be a thickener or a gelforming agent. Preferred thickener and gel forming agents are thickening polymers. The amount of viscosity modifying agent can be, for example, from about 0.01% to about 20%, or from about 0.05% to about 10%, or from about 0.1% to about 5% by weight based on the total composition. Preferred are thickening polymers, for example, copolymers of at least one first type of monomers selected from acrylic acid and methacrylic acid and at least one second type of monomers selected from esters of acrylic acid with ethoxylated fatty alcohols; cross-linked polyacrylic acid; cross-linked copolymers of at least one first type of monomers selected from acrylic acid and methacrylic acid and at least one second type of monomers selected from esters of acrylic acid with C10- to C30-alcohols; copolymers of at least one first type of monomers selected from acrylic acid and methacrylic acid and at least one second type of monomers selected from esters of itaconic acid with ethoxylated fatty alcohols; copolymers of at least one first type of monomers selected from acrylic acid and methacrylic acid and at least one second type of monomers selected from esters of itaconic acid with ethoxylated C10- to C30-alcohols and at least one third type of monomers selected from C1- to C4-aminoalkylacrylates; copolymers of two or more monomers selected from acrylic acid, methacrylic acid, acrylic acid esters and methacrylic acid esters; copolymers of vinylpyrrolidon and ammonium acryloyl dimethyltaurate; copolymers of ammonium acryloyl dimethyltaurate and monomers selected from esters of methacrylic acid with ethoxylated fatty alcohols; hydroxyethylcellulose; hydroxypropylcellulose; hydroxypropylguar; glyceryl polyacrylate; glyceryl polymethacrylate; copolymers of at least one C2-, C3-, or C4-alkylene and styrene; polyurethanes; hydroxypropyl starch phosphate; polyacrylamide; copolymer of maleic anhydride and methylvinylether crosslinked with decadien; locust bean gum; guar gum, xanthan; dehydroxanthan; carrageenan; karaya gum; hydrolysed corn starch; copolymer of polyethylenoxide, fatty alcohols and saturated methylene diphenyl diisocyanate (e.g., PEG-150/Stearylalkohol/SMDI Copolymer).

Most preferred thickeners are amphiphilic polymers. Amphiphilic polymers comprise at least one hydrophilic group and at least one hydrophobic group, e.g., a fatty chain. A fatty chain can be for example a hydrocarbon group with from about 8 to about 30 or from about 10 to about 22 carbon atoms. The amphiphilic polymers can be associative thickeners. They can be ionic or nonionic, wherein anionic and nonionc polymers are preferred. Amphiphilic polymers are, for example:

(1) copolymers of acrylic- or methacrylic acid and monomers comprising at least one fatty chain; e.g.,
  crosslinked acrylic acid/C10-30-alkylacrylate copolymer, e.g., Pemulen® TR1, Pemulen® TR2, Carbopol® 1382, Carbopol® 1342, Carbopol® ETD 2020;
  (meth)acrylic acid/ethyl acrylate/alkylacrylate copolymer, e.g., Acusol® 823, Imperon R®V;
  crosslinked acrylic acid/vinyl isododecanoate copolymer, e.g., Stabylen® 30;
  acrylic acid/vinylpyrrolidone/lauryl methacrylate terpolymer, e.g., Acrylidone LM®, ACP-1184®, ACP-1194®;
  acrylic acid/lauryl(meth)acrylate copolymer, e.g., Coatex SX®g;
  (meth)acrylic acid/alkyl acrylate/alkyl(polyethoxy)allylether, e.g., Rheovis® CR, CR3, CR2, and CRX;
  methacrylic acid/ethyl acrylate/stearyl(polyethoxy)allyl ether, e.g., Salcare® SC90 and SC80;
  (meth)acrylic acid/ethylacrylate/polyethoxylated lauryl acrylate terpolymer, e.g., Rheo 2000®;
  methacrylic acid/ethylacrylate/polyethoxylated stearyl methacrylate terpolymer, e.g., Acrysol® 22, Acrysol® 25, and DW-1206A of Rhom&Haas;
  methacrylic acid/polyethoxylated nonylphenolacrylate copolymer, e.g., Rheo 3000®;
  acrylic acid/polyethoxylated stearyl- or cetylmonoitaconate, e.g., Structure® 2001 or 3001;
  copolymers of methacrylic acid, butylacrylate and a hydrophobic monomer with at least one fatty chain, e.g., 8069-146A of National Starch;
  terpolymers of acrylic acid/C15-alkylacrylate/polyethylenglykol acrylate (28 mol ethylenoxide), e.g., Dapral GE 202®;
  partial fatty acid ester salts of copolymers of acrylic acid/dimethylethanolamin, e.g., Dapral GE 202 DMA®;
  copolymers of acrylic acid, acrylate and an amphiphilic monomer comprising a fatty chain with a urethan group, e.g., Additol VXW 1312®;
  acrylate copolymers modified with fatty chain hydrophobic groups, e.g., Acusol 102®;
(2) polysaccharides, modified with groups containing at least one fatty chain, e.g.,
  cellulose modified with groups containing at least one fatty chain, alkyl-, arylalkyl- or alkylaryl groups, wherein the alkyl groups have 8 to 22 C-atoms;
  nonionic alkyl hydroxyethyl cellulose, e.g., Natrosol® Plus Grade 330 CS, Polysurf® 67, and ADX 401 (C16-alkyl) of Aqualon;
  quaternized alkyl hydroxy alkyl cellulose, e.g., Quatrisoft® LM 200, Quatrisoft® LM-X 529-18-A, Quatrisoft® LM-X 529-18-B (C12-Alkyl), Quatrisoft® LM-X 529-8 (C18-Alkyl), Crodacel® QM, Crodacel® QL (C12-Alkyl), Cordacel® QS (C18-Alkyl);
  nonionic nonoxynyl hydroxyethyl cellulose, e.g., Amercell® HNM-1500;
  nonionic alkyl cellulose, e.g., Bermocellg EHM 100;
  poly-C12-18-alcohol saccharide, e.g., Emulsan®, Biosan® LPS-50;
  hydroxyalkyl guar gum modified with a fatty chain, e.g., Esaflor® HM 22 (C22-Alkyl modified), Miracare® XC 95-3 (C14-alkyl modified), RE 205-146 (C20-alkyl modified) of Rhone-Poulenc,
(3) copolymers of maleic anhydride and monomers containing at least one fatty chain, e.g.,
  N-octadecylvinylether/maleic anhydride copolymer, e.g., Gantrez® AN-8194
  Vinylacetate/IsobutylmonomaleateNinylneodecanoate terpolymer, e.g., ACV-4033 or 9649-147 of ISP, Meypro-Fix 509®, Densodrin® BA, Lipoderm Liquor FP;
(4) polyurethanes and their derivatives, containing groups with at least one fatty chain, e.g., Rheolate® 204, 205, 208, 210, 255, or 278; Bermodol Pur® 2130; Acrysol® SCT-275, Acrysol® RM-870, Acrysol® RM-825, Acrysol® 44, Acrysol 46®, DW-1206 B, DW-1206 F, SW-1206 G, and DW-1206 J of Rohm & Haas; Dapral® T 212, SER-AD FX 1100, Borchigel® L.75.N;

(5) copolymers of crotonic acid and monomers containing at least one fatty chain, e.g., Vinylacetate/Crotonic acid/Allylstearate terpolymer;

(6) copolymers of N-Vinylpyrrolidone and monomers containing at least one fatty chain, e.g., alkyl substituted polyolefins containing long-chain hydrocarbon groups, e.g., Antaron® V216 or Antaron® V220 of ISP;

(7) nonionic copolymers of acrylic- or methacrylic acid alkylester with C1-6-alkyl groups and amphiphilic monomers with fatty chain, e.g., copolymers of methylmethacrylate and polyethoxylated stearylacrylate, e.g., Antil® 208;

(8) nonionic copolymers of hydrophilic acrylates or methacrylates and hydrophobic monomers with fatty chain, e.g., copolymers of polyethylenglykol methacrylate and alkylmethacrylate.

Most preferred amphiphilic polymers are copolymers of acrylic acid or methacrylic acid and alkylesters of acrylic acid or methacrylic acid, especially crosslinked acrylic acid/C10-30-alkyl acrylate copolymers, e.g., Pemulen® TR1, Pemulen® TR2, Carbopol® 1382, Carbopol® 1342, Carbopol® ETD 2020 with INCI-name Acrylates/C10-30 Alkyl Acrylate Crosspolymer.

Optional Ingredients

The composition according to the invention can also contain conventional cosmetic additives usually used in hair treatment compositions in addition to the above-mentioned ingredients, e.g., fragrances and perfume oils in an amount of for example up to about 2% by weight, preferably from about 0.01% to about 1% by weight; preservatives such as, for example, parabenes, phenoxetol, iodopropynyl carbamate, parahydroxybenzoic acid ester, benzoic acid, salicylic acid, sorbic acid, mandelic acid, polyhexamethylene biguanidine hydrochloride, or isothiazoline based compounds in an amount of for example up to about 2% by weight, preferably from about 0.01% to about 1% weight; hair care substances, such as, e.g., betaine, panthenol, plant extracts, vegetable extracts, protein hydrolysates and silk hydrolysates, lanolin derivatives, in an amount of for example from about 0.01% to about 5%, preferably from about 0.1% to about 4% by weight; cosmetic dyestuffs in an amount of up to about 6% by weight, preferably from about 0.1% to about 4% by weight, e.g., C.I. Pigment Red 4 (C.I. 12 085), C.I. Pigment Green (C.I. 74 260), and/or C.I. Vat Blue 4 (C.I. 69 800); pigments or pearlescent pigments in an amount of, for example, from about 0.01% up to about 25% by weight, preferably from about 1% to about 20% by weight, e.g., those with a titanium dioxide/mica base; light protective agents, antioxidants, radical-trapping agents, anti-dandruff agents; vitamines; luster-imparting substances, and combability-improving substances in amounts of from about 0.01% to about 2% by weight.

Method of Making

The compositions of the present invention can be made by conventional formulation and mixing techniques. The cream products in the form of emulsions can be made by emulsification of aqueous phase and fatty phase, preferably done at elevated temperatures of for example 80° C. to 100° C. Volatile ingredients such as fragrances are added preferably at lower temperatures for example at 50° C. to 70° C. The emulsified composition is filled into the final packaging when still in a fluid state at temperatures above room temperature, for example at 50° C. to 70° C. The compositions become non-fluid or semi-solid after cooling to room temperature. The final packaging can be a transparent or translucent package.

Method Of Use

An embodiment of the invention is a method of hair treatment, said method comprising the steps of:

a) providing a hair styling cream as described in detail above;

b) applying the composition to hair; and c) setting or putting the hair in a hair style without subsequent rinsing.

Such method generally involves application of an effective amount of the product to dry, slightly damp, or wet hair preferably before the hair is arranged to a desired style. The composition is then dried or allowed to dry. By "effective amount" is meant an amount sufficient to provide the hair hold, hair shine, and/or hair style benefits desired considering the length and texture of the hair. In general, from about 0.5 g to about 50 g of product will be applied to the hair, depending upon the particular product formulation, length of hair, and type of hair style. The product can be applied to the hair at least partially in form of at least one thread or preferably a multitude of threads like a spider web. To produce the threads prior to application to the hair, the creamy product is taken out of a suitable packaging, e.g., a tube or a screwable jar and distributed between the fingers or between the palms of the hands by rubbing. After a few seconds during the drying period (i.e., when evaporation of some of the volatile components such as water has started but has not yet been completed) the fingers or the hands are hold together and then drawn apart forming threads.

Compositions of the type of the exemplary compositions described below will have benefits over conventional hair styling cream products, in one or more of good rope-, thread-, or fiber forming effect with a more pleasant, less sticky and less greasy or oily feeling to the touch during application and/or after working into the hair; in addition to good hair stability, hair definition, hair hold, or hair gloss.

EXAMPLES

The compositions illustrated in the following examples illustrate specific embodiments of the hair styling compositions of the present invention, but are not intended to be limiting thereof. Other modifications can be undertaken by the skilled artisan without departing from the spirit and scope of this invention. These exemplified embodiments of the hair styling composition of the present invention provide styling and shine benefits, good rope-, thread-, or fiber forming effects with an especially pleasant, non-sticky, powdery feeling. The compositions illustrated in the following examples are prepared by conventional formulation and mixing methods. All exemplified amounts are listed as weight percents and exclude minor materials such as diluents, preservatives, color solutions, imagery ingredients, botanicals, and so forth, unless otherwise specified. If a trade name is mentioned as ingredient and the respective product is itself a mixture (e.g., a solution, emulsion, dispersion, etc.), then the exemplified amount relates to this mixture, unless otherwise specified.

Example 1

| | |
|---|---|
| 9 | Stearyl alcohol |
| 9 | Petrolatum (vaseline) |
| 1.5 | Ceteareth-25 |
| 3 | Polawax ® GP 200 [1] |
| 2 | Polyvinylpyrrolidone (Luviskol ® K90) |
| 4 | Propylene glycol |
| 5 | PEG-12 |
| 3 | Bis-PEG-12 Dimethicone Beeswax (Siliconyl Beeswax) |
| 16 | Dow Corning 9040 Silicone Elastomer [2] |
| balance to 100 | Water |

[1] 80:20 mixture of cetearyl alcohol/PEG-20 stearate
[2] Dimethicone Crosspolymer, 12% in cyclopentasiloxane

Example 2

| | |
|---|---|
| 0.15 | Acrylates/C10-30 Alkyl Acrylate Crosspolymer (Carbopol ® 1382) |
| 0.12 | Aminomethylpropanol (95%) |
| 10 | Stearyl alcohol |
| 10 | Petrolatum (vaseline) |
| 1.5 | Ceteareth-25 |
| 0.3 | PEG-40 hydrogenated castor oil |
| 3 | Polawax ® GP 200 [1] |
| 12 | Luviskol ® K85 (Polyvinylpyrrolidone, 20% in water) |
| 4 | Propylene glycol |
| 5 | PEG-12 |
| 4 | Bis-PEG-12 Dimethicone Beeswax (Siliconyl Beeswax) |
| 18 | Dow Corning 9040 Silicone Elastomer [2] |
| 1.0 | Phenoxetol |
| 0.4 | Methylparaben, Propylparaben |
| 0.3 | Fragrance |
| balance to 100 | Water |

[1] 80:20 mixture of cetearyl alcohol/PEG-20 stearate
[2] Dimethicone Crosspolymer, 12% in cyclopentasiloxane

Example 3

| | |
|---|---|
| 10 | Disiloxan (Dow Corning 200 Fluid/0.65 cSt) |
| 9 | Stearyl alcohol |
| 9 | Petrolatum (vaseline) |
| 1.5 | Ceteareth-25 |
| 1.0 | PEG-40 hydrogenated castor oil |
| 3 | Polawax ® GP 200 [1] |
| 3 | Polyvinylpyrrolidone (Luviskol ® K90) |
| 4 | Propylene glycol |
| 5 | PEG-12 |
| 3 | Bis-PEG-12 Dimethicone Beeswax (Siliconyl Beeswax) |
| 16 | Dow Corning 9040 Silicone Elastomer [2] |
| 1.0 | Phenoxetol |
| 0.4 | Methylparaben, Propylparaben |
| 0.3 | Fragrance |
| balance to 100 | Water |

[1] 80:20 mixture of cetearyl alcohol/PEG-20 stearate
[2] Dimethicone Crosspolymer, 12% in cyclopentasiloxane

Comparative Example A

| | |
|---|---|
| 0.15 | Acrylates/C10-30 Alkyl Acrylate Crosspolymer (Carbopol ® 1382) |
| 0.12 | Aminomethylpropanol (95%) |
| 5.0 | Polawax ® GP 200 |
| 1.5 | Ceteareth-25 |
| 0.4 | Methylparaben, Propylparaben |
| 1.0 | Phenoxetol |
| 0.3 | Fragrance |
| 1.0 | PEG-40 hydrogenated castor oil |
| 3.5 | Polyvinylpyrrolidone (e.g., Luviskol ® K90) |
| 4.0 | Propylene glycol |
| 18.0 | Lanolin Alcohol |
| 11.0 | Lanolin |
| 2.0 | Compritol ® 888 [3] |
| 2.0 | Emulgrade ® SE-PF [4] |
| 17.0 | Dow Corning 9040 Silicone Elastomer |
| balance to 100 | Water |

[3] Glyceryl Dibehenate/Tribehenin/Glyceryl Behenate 50/35/15
[4] Glyceryl Stearate/Ceteareth-20/Cetearyl Alcohol/Cetylpalmitate/Ceteareth-12

Comparative Example B

| | |
|---|---|
| 29.0 | Mineral Oil (Paraffinum Perliquidum) |
| 18.0 | Ceresin (Polycerin 1894) |
| 8.0 | Triceteareth-4 Phosphate (Hostaphat KW 340 D) |
| 3.0 | PEG-25 Hydrogenated Castor Oil |
| 8.0 | Sucrose Polybehenate (Sefose-2275) |
| 4.0 | Beeswax |
| 15 | Luviskol ® K85 (Polyvinylpyrrolidone, 20% in water) |
| 0.2 | Propylparaben |
| 0.4 | Fragrance |
| 1.0 | PEG-40 hydrogenated castor oil |
| 18.0 | Dow Corning 9040 Silicone Elastomer |

Comparative Example C

| | |
|---|---|
| 1.0 | Carbomer |
| 0.8 | Aminomethylpropanol (95%) |
| 0.5 | Fragrance |
| 4.0 | Propylene glycol |
| 0.4 | Methylparabene |
| 1.0 | PEG-40 hydrogenated castor oil |
| 15.0 | Dow Corning 9040 Silicone Elastomer |
| balance to 100 | Water |

Comparative Example D

| | |
|---|---|
| 1.0 | Carbomer |
| 0.8 | Aminomethylpropanol (95%) |
| 0.5 | Fragrance |
| 4.0 | Propylene glycol |
| 0.4 | Methylparabene |
| 1.0 | PEG-40 hydrogenated castor oil |

-continued

| | |
|---|---|
| 4.0 | Hair fixing polymer (PVP and VP/VA Copolymer) |
| 20.0 | Dow Corning 9040 Silicone Elastomer |
| balance to 100 | Water |

Comparative Example E

| | |
|---|---|
| 10.0 | Stearyl alcohol |
| 10.0 | Petrolatum (vaseline) |
| 1.5 | Ceteareth-25 |
| 0.4 | Methylparabene, propylparabene |
| 1.0 | Phenoxetol |
| 0.3 | Fragrance |
| 1.0 | PEG-40 hydrogenated castor oil |
| 4 | Polyvinylpyrrolidone (Luviskol ® K90) |
| 3.0 | Polawax ® GP 200 |
| 4.0 | Propylene glycol |
| 5.0 | PEG-12 |
| 4.0 | Bis-PEG-12 Dimethicone Beeswax (Siliconyl Beeswax) |
| balance to 100 | Water |

Compositions 1 to 3 and comparative compositions A to E have been evaluated for their thread-forming effects. The creamy products can be taken out of suitable screwable jars with the fingers and distributed between the fingers or between the palms of the hands by rubbing. After a few seconds during the drying period (i.e., when evaporation of some of the volatile components such as water has started but has not yet been completed) the fingers or the hands are hold together and then drawn apart. Threads can be formed from compositions 1 to 3, but not from comparative compositions A to E.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair styling cream comprising
    (a) from about 10% to about 25% by weight of crosslinked silicone polymer; wherein the crosslinked silicone copolymer is a dimethicone crosspolymer cross linked with $C_3$ to $C_{20}$ alkyl groups;
    (b) from about 8% to about 20% by weight of two alkoxylated compounds, wherein one alkoxylated compound is polyethylenoxides with a molecular weight in the range of from 500 to 700 and the other alkoxylated compound is fatty acid esters of bis-(polyethylenoxide)polydimethylsiloxane wherein the weight ratio of crosslinked silicone copolymer to the sum of alkoxylated compound is from about 1:2 about 1:6
    (c) from about 0.5% to about 5% by weight of emulsifier; wherein the emulsifier is nonionic wherein the nonionic emulsifier is ethoxylated hydrogenated castor oil;
    (d) a fatty phase; and
    (e) an aqueous phase comprising from about 20% to about 50% by weight water, and further comprising from about 1% to about 18% by weight of nonionic hair fixing polymer wherein the nonionic hair fixing polymer is selected from the group consisting of polyvinylpyrrolidone, copolymers of vinyl pyrrolidone and vinyl acetate or copolymers of vinylpyrrolidone, methacrylamide, and vinylimidazole.

2. A hair styling cream according to claim 1, wherein said fatty phase (d) comprises at least one fat, oil or wax compound in an amount of from about 5% to about 60% by weight based on the total composition and wherein said fat, oil or wax compounds are selected from the group consisting of hydrocarbon compounds, fatty alcohols, fatty acid triglycerides, and silicone oils.

3. A hair styling cream according to claim 1, wherein the aqueous phase further comprises at least one mono- or polyhydric alcohol from 1 to 5 carbon atoms.

4. A hair styling cream according to claim 1, wherein the pH is from 6 to 8.

5. A method of hair treatment, said method comprising the steps of:
    (a) providing a hair styling cream according to claim 1;
    (b) applying the cream composition to hair; and
    (c) setting or putting the hair in a hair style without subsequent rinsing.

\* \* \* \* \*